United States Patent [19]

Wang et al.

[11] Patent Number: 5,530,145

[45] Date of Patent: Jun. 25, 1996

[54] ANTICHOLESTEREMIC COMPOUNDS

[75] Inventors: Hui-Po Wang; On Lee, both of Taipei; Chin-Tsai Fan, Hsin-Ying, all of Taiwan

[73] Assignee: Syn-Tech Chem & Pharm Co., Ltd., Taiwan

[21] Appl. No.: 350,425

[22] Filed: Dec. 6, 1994

Related U.S. Application Data

[63] Continuation-in-part of Ser. No. 259,537, Jun. 14, 1994, Pat. No. 5,412,112.

[51] Int. Cl.$^6$ ............................. C07C 69/76; C07C 59/48
[52] U.S. Cl. ............................. 549/328; 549/329; 560/61; 560/60; 560/62; 560/45; 562/470; 562/471; 546/290; 546/303; 564/182; 558/241; 558/257
[58] Field of Search ..................... 549/328, 329; 560/60, 61, 62, 48; 562/470, 471; 546/303, 290; 564/182; 558/241, 257

[56] References Cited

U.S. PATENT DOCUMENTS

| | | | |
|---|---|---|---|
| 3,674,836 | 7/1972 | Creger | 260/473 G |
| 3,707,566 | 12/1972 | Creger et al. | 260/613 D |
| 4,665,226 | 5/1987 | Kearney | 562/471 |

OTHER PUBLICATIONS

Stevens, T. J. et al Artery (Fulton, Mich.) (1983) 12(2) 81–94.

Sircar et al., "Phenylenebis(oxy)bix[2,2–dimethylpentanoic acid's: Agents That Elevate High–Density Lipoproteins,", J. Med. Chem 26:1020–1027, 1983.

Morishita et al., "Synthesis and Hypolipidemic Activity of 2–Substituted Isobutyric Acid Derivatives," J. Med. Chem. 31:1205–1209, 1988.

*Primary Examiner*—Paul J. Killos
*Attorney, Agent, or Firm*—Fish & Richardson

[57] ABSTRACT

Novel anticholesteremic compounds capable of reducing blood cholesterol levels. Also included in this invention are (i) intermediates from which the abovementioned anticholesteremic compounds can be prepared, and (ii) methods for preparing both the intermediates and the anticholesteremic compounds.

20 Claims, No Drawings

ANTICHOLESTEREMIC COMPOUNDS

This application is a continuation-in-part of U.S. patent application Ser. No. 08/259,537, filed Jun. 14, 1994, now U.S. Pat. No. 5,412,112.

BACKGROUND OF THE INVENTION

The present invention relates to a series of compounds capable of reducing blood cholesterol levels. More particularly, the present invention concerns a series of novel gemfibrozil analogues.

5-(2,5-Dimethylphenoxy)-2,2-dimethylpentanoic acid, which is also known as gemfibrozil, has the following structure:

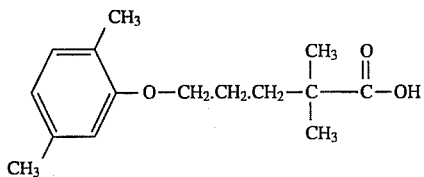

Gemfibrozil is capable of reducing blood cholesterol levels. There are several reported syntheses of gemfibrozil and certain analogues. For example, U.S. Pat. No. 3,674,836 (1972) discloses gemfibrozil and its analogues thereof, as well as a process for preparing them. U.S. Pat. No. 3,707,566 (1987) discloses a process for preparing gemfibrozil.

SUMMARY OF THE INVENTION

The present invention relates to a novel method for synthesizing a series of anticholesteremic compounds.

The anticholesteremic compounds of this invention may be represented by general formula (I) set forth below:

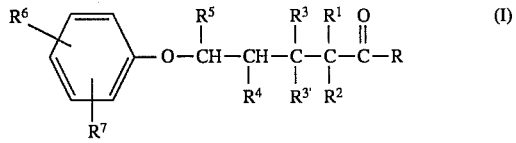

wherein R is hydroxy, $C_1$–$C_8$ alkoxy, phenoxy, $C_1$–$C_4$ alkylthio, phenylthio, amino, $C_1$–$C_4$ alkylamino, phenylamino, benzylamino, or pyridyl-3-methoxy; each of $R^1$ and $R^2$ independently is hydrogen or $C_1$–$C_4$ alkyl; $R^3$ is $C_1$–$C_8$ alkoxy, $C_1$–$C_5$ acyloxy, pyridyl-3-methoxy, $C_1$–$C_4$ alkylthio, phenylthio, amino, $C_1$–$C_4$ alkylamino, phenylamino, benzylamino, $C_2$–$C_5$ alkylacyl, or $C_7$–$C_{10}$ phenylacyl,

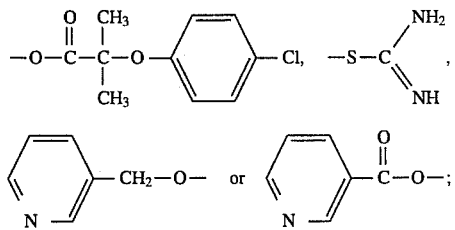

each of $R^3$, $R^4$ and $R^5$ independently is hydrogen or $C_1$–$C_4$ alkyl; each of $R^6$ and $R^7$ independently is hydrogen, hydroxy, halogen, $C_1$–$C_8$ alkyl, $C_1$–$C_8$ alkoxy, $C_1$–$C_8$ acyl, or $C_1$–$C_8$ alkylamino.

Also included in this invention are (i) novel intermediates from which the above-described anticholesteremic compounds can be prepared, and (ii) methods for preparing both the intermediates and the anticholesteremic compounds. The details are set forth immediately below. the preferred embodiments, and also from the appending claims.

DETAILED DESCRIPTION OF THE INVENTION

The present invention of racemic compounds of general formula (I) can be prepared from novel intermediates of general formula (II):

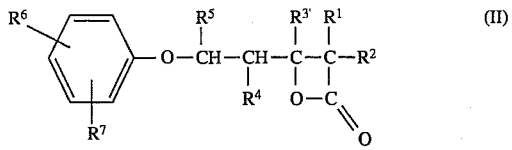

wherein $R^1$, $R^2$, $R^3$, $R^4$, $R^5$, $R^6$ and $R^7$ are defined as above.

The methods for the preparation of compounds of general formula (I) from intermediates of general formula (II) are shown in the following Scheme 1, wherein $R^1$, $R^2$, $R^3$, $R^{3'}$, $R^4$, $R^5$, $R^6$ and $R^7$ are defined as above; $R^a$ is hydrogen, $C_1$–$C_8$ alkyl, phenyl, $C_7$–$C_{10}$ phenylalkyl, or $C_7$–$C_{10}$ alkylphenyl; and X is a halogen, i.e., fluoro, chloro, bromo, or iodo. In accordance with Scheme 1, the compounds of general formula (I) are prepared by reacting an intermediate of general formula (II) with (1) $C_1$–$C_8$ alkyl alcohol, $C_1$–$C_4$ alkylthiol, thiophenol, ammonia, $C_1$–$C_8$ alkylamine, aniline, benzylamine, $C_1$–$C_9$ aliphatic acid, thiourea, 3-hydroxymethyl pyridine, nicotinic acid, or $C_7$–$C_{11}$ phenylaliphatic acid or $C_7$–$C_{11}$ alkylbenzoic acid, in the presence of solvents such as aliphatic alcohol (propyl alcohol or n-butyl alcohol) or alkyl benzene (e.g., toluene or dimethyl benzene), at –10° C.–150° C.; or (2) sodium borohydride in a polar aprotic solvent such as tetrahydrofuran, 1,2-dimethoxy ethane or dimethylformamide.

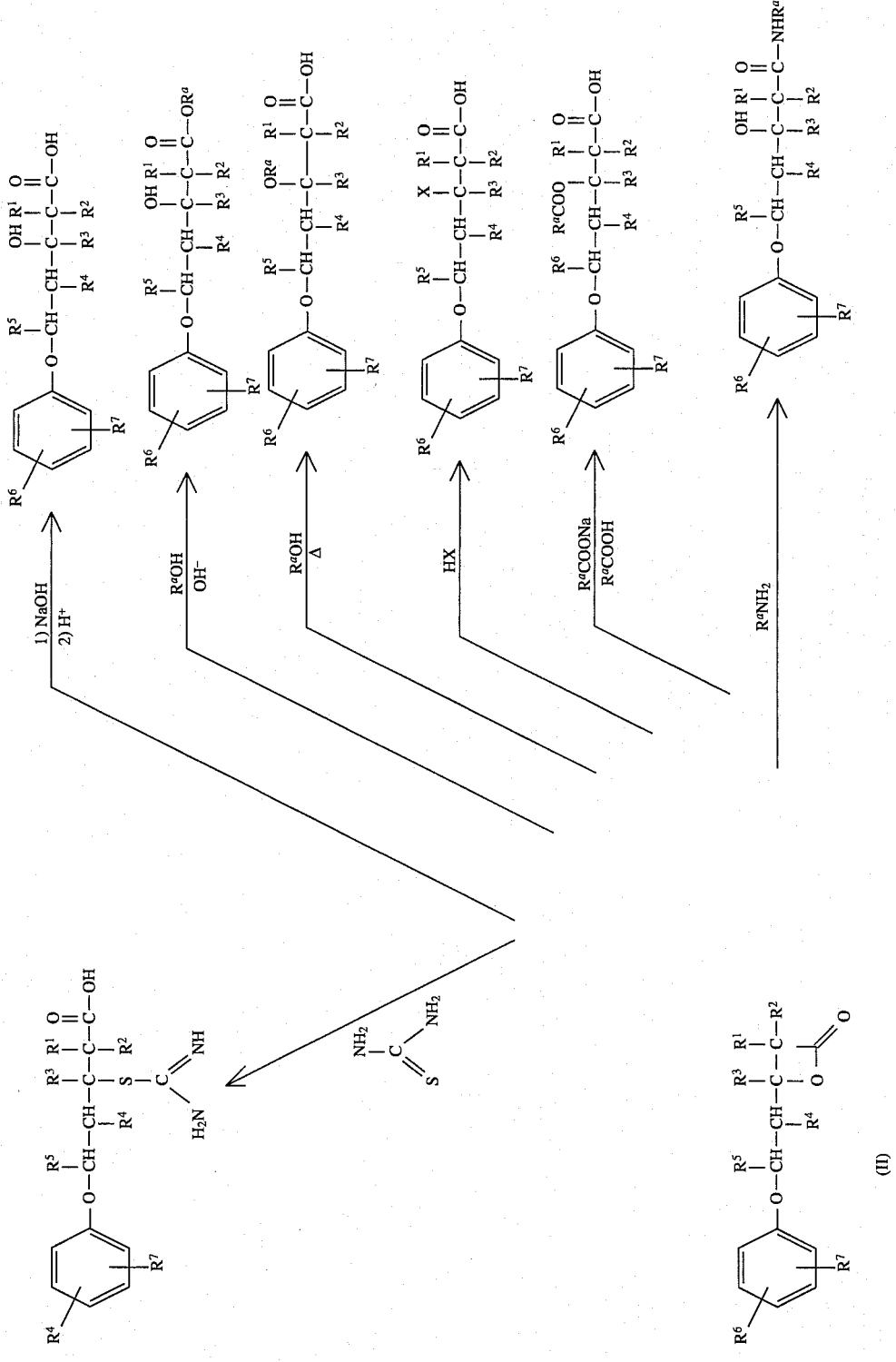
Scheme 1

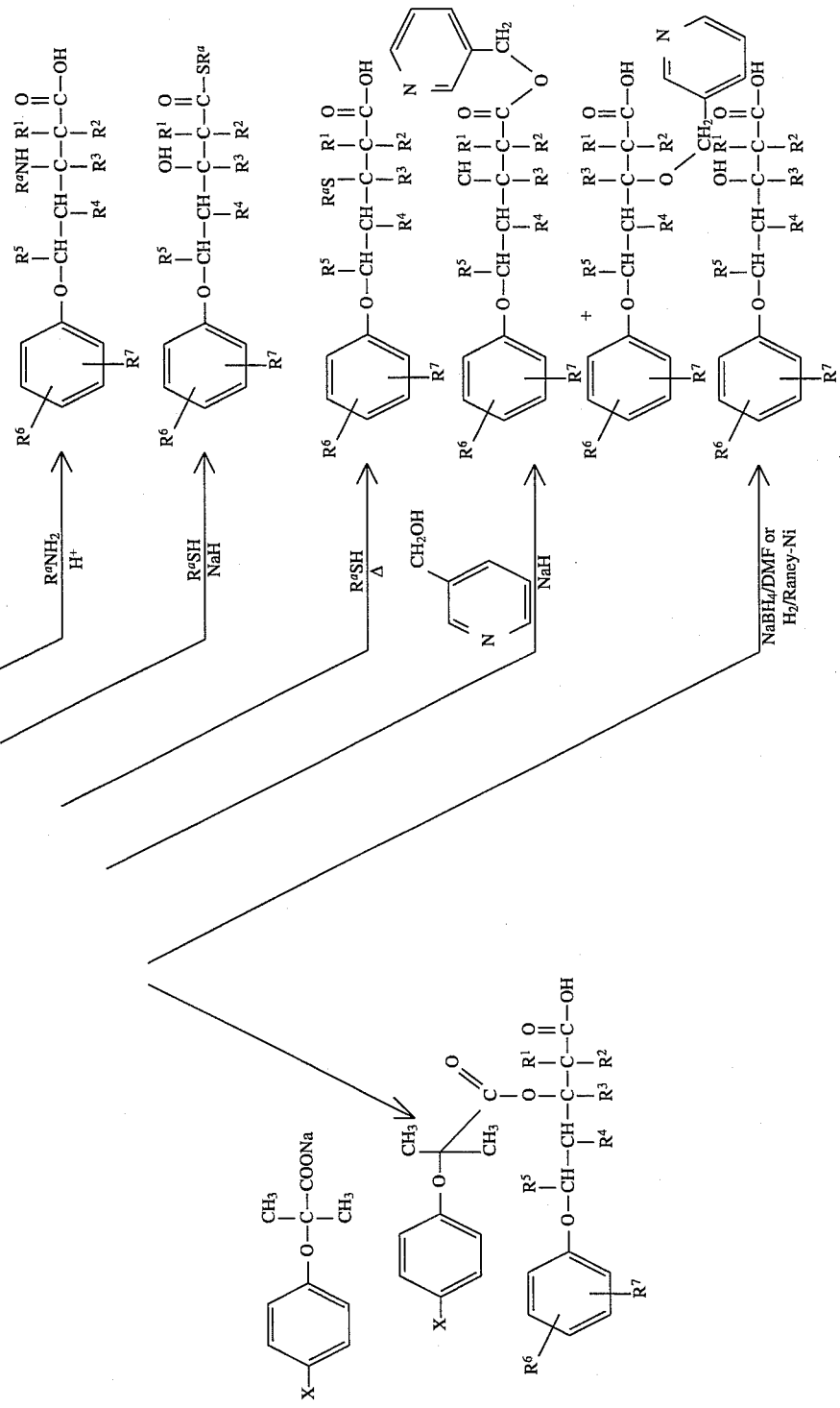

The intermediates of general formula (II) can be prepared according to Scheme 2:

Scheme 2

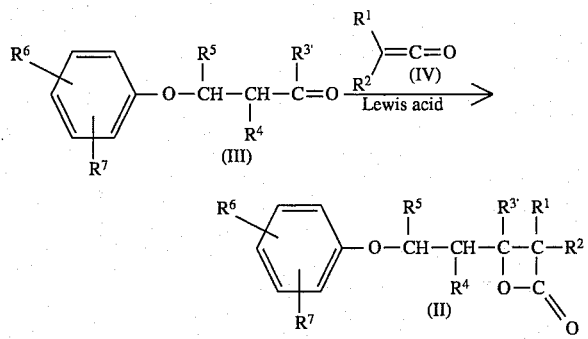

wherein $R^1$, $R^2$, $R^3$, $R^4$, $R^5$, $R^6$ and $R^7$ are defined as above. In accordance with Scheme 2, the intermediates of general formula (II) are prepared by reacting the compounds of general formula (III) with ketenes (IV), for example, $C_3$–$C_6$ alkylketene or $C_4$–$C_{10}$ dialkylketene in the presence of Lewis acid, such as zinc (II) chloride, aluminum (III) chloride, iron (III) chloride, titanium (IV) chloride, titanium (IV) tetraalkoxide, boric acid, boron trifluoride, trialkyl borate, zirconium (IV) tetrachloride or zirconium (IV) tetralkoxide, in aprotic organic solvent, for example dichloromethane, carbon tetrachloride, methyl acetate, ethyl acetate or 1,2-dimethoxy ethane or in polar aprotic solvent, such as hexamethylphosphoramide, N,N-dimethylformamide, dimethylsulfoxide or N,N-dimethylacetamide at –50° C.–175° C. The ketenes of general formula (IV) and the compounds of general formula (III) are known compounds, which can be prepared using well-known synthetic methods.

Without further elaboration, it is believed that one skilled in the art can, based on the description herein, utilize the present invention to its fullest extent. The following specific embodiments are, therefore, to be construed as merely illustrative, and not limitative of the remainder of the disclosure in any way. Note that compounds 1–12 correspond to those prepared following the procedures described in Examples 1–12, respectively.

Example 1

Synthesis of 5-(2,5-dimethylphenoxy)-3-hydroxy-2,2,3-trimethylpentanoic acid β-lactone 4-(2,5-Dimethylphenoxy)-butane-2-one (192 mg, 1 mmol) was dissolved in 50 ml ethyl acetate. Five grams of anhydrous magnesium sulfate were added and the mixture was stirred for 10 min. The magnesium sulfate was filtered and to the filtrate was added 0.005 mmol zinc chloride and 77 mg (1.1 mmol) dimethylketene. After 48 hours the ethyl acetate solution was washed with 2×20 ml of water and with 2×20 ml 5% aqueous sodium bicarbonate solution. The ethyl acetate layer was dried with anhydrous sodium sulfate and filtered. The filtrate was concentrated on a rotary evaporator to yield an oil product, which was recrystallized from n-hexane to yield 50 mg of the product as a solid, mp 93.5° C.~94.5° C. IR(KBr): 3100, 2980, 2945, 2895, 1800, 1615, 1590, 1510 cm$^{-1}$; $^1$H NMR (80 MHz, CDCl$_3$): δ1.34–1.40(6H, d, O–C(CH$_3$)–C(CH$_3$)2C=O), 1.58(3H, s, O–C(CH$_3$)–C(CH$_3$)$_2$C=O), 2.15 (3H, s, Ar–CH$_3$), 2.30 (3H, s, Ar–CH$_3$), 2.33 (2H, t, Ar–O–CH$_2$–CH$_2$–), 4.09(2H, t, Ar–O–CH$_2$), 6.62, 6.71, 6.95, 7.05(3H, m, Ar–H) ppm; Mass m/z (rel. inten.): 262(58, M+), 192(10), 174(13), 134(10), 122(100), 97(78), 69(21), 55(64)

Example 2

Synthesis of 5-(2,5-dimethylphenoxy)-3-hydroxy-2,2,4-trimethylpentanoic acid β-lactone 3-(2,5-Dimethylphenoxy)-2-methylpropionaldehyde (7.6914 g, 0.04 mole) and zinc chloride (0.002 mol) were dissolved in 150 ml ethyl acetate, and the solution was kept at 4° C. Dimethylketene (2.8 g, 0.04 mol) was added and stirred for 36 hours. The solution was washed subsequently with 150 ml of water, 50 ml 1 M sodium carbonate aqueous solution, and 100 ml saturated sodium chloride solution. The ethyl acetate layer was dried with anhydrous sodium sulfate and filtered. The filtrate was concentrated on a rotary evaporator to yield a crude product (10 g, 99% yield). The crude product was recrystallized from n-hexane to yield 7.34 g of the product as a solid (yield 73%). IR (KBr): 3071–2881, 1827(Vc=c), 1614, 1585, 1511, 1473, 1465, 1430, 1404, 1394 cm$^{-1}$; $^1$H NMR (80 MHz, CDCl$_3$): δ1.05–1.45 (9H, M, –CH$_3$), 2.32(3H, s, Ar–CH$_3$), 2.41(3H, s, Ar–CH$_3$), 2.0–2.61(1H, m, –CH$_2$–CH(CH$_3$)–CH$_2$–), 3.85–3.91(2H, d, Ar–CH$_2$), 4.22–4.35(1H, d, –COO–CH–), 6.41, 6.74, 7.00, 7.07(3H, m, Ar–H) ppm; Mass m/z (rel. inten.): 262(18, M+)135(6), 122(100), 97(50), 70(20), 55(30).

Example 3

Synthesis of 2,2-dimethyl-5(2,5-dimethylphenoxy)-3-hydroxyhexanoic acid β-lactone 3-(2,5-Dimethylphenoxy)-butanaldehyde (19.23 g, 0.1 mol) and 5 mmol of zinc chloride were dissolved in 250 ml of ethyl acetate. The temperature was kept at 4° C. then 7.01 g (0.1 mol) of dimethylketene was added. After stirring for 48 hours, the reaction mixture was treated using the same procedure as in example 2 to yield 22.23 g of the crude product. The crude product was purified by column chromatography to give a liquid (20 g). Recrystallization from n-pentane afforded the product as a solid, mp 36.5°–38.5° C. IR (KBr): 3046–2877, 1823(Vc=o), 1615, 1583, 1506, 1463 1412, 1392, 1380, 1311, 1285, 1260 cm$^{-1}$; $^1$H NMR (80 MHz, CDCl$_3$):δ1.25–1.5(9H, m, –CH$_3$) 1.99–2.2(2H, m, –CH$_2$–), 2.15(3H, s, Ar–CH$_3$), 2.29(3H, s, Ar–CH$_3$), 4.4–4.71(2H, m, Ar–O–CH(CH$_3$)–, –COO–CH–), 6.63, 6.71, 6.90, 7.06 (3H, m, Ar–H) ppm; Mass m/z (rel. inten.): 262 (17 M+), 149(13), 122(73), 107(40), 97(53), 70(92), 42(100).

Example 4

Synthesis of 2,2-diethyl-5-(2,5-dimethylphenoxy)-3-hydroxypentanoic acid β-lactone 3-(2,5-Dimethylphenoxy)-propionaldehyde (2.54 g, 0.014 mol) was dissolved in 200 ml ethyl acetate. Zinc chloride (0.1 mmol) and dimethylketene (2.8 g, 0.04 mol) were added and the temperature was kept at 4° C. After stirring for 48 hours, the ethyl acetate solution was partitioned first with 2×100 ml of water and then with 2×100 ml of 5% aqueous sodium bicarbonate solution. The ethyl acetate layer was dried with anhydrous sodium sulfate and then filtered. The filtrate was concentrated by rotary evaporation and the residue was purified by column chromatography to yield a liquid product. Recrystallization from n-hexane afforded a 2.51 g of the product (63% yield); m.p. 56°–56.5° C. 1H NMR (80 MHz, CDCl$_3$): δ0.85–1.15(6H, m, –C(CH$_2$CH$_3$)2–COO–), 1.4–2.0(4H, m, −C(CH$_2$CH$_3$)2−COO−), 2.17 (3H, s, Ar−CH$_3$), 2.30 (3H, s, Ar−CH$_3$), 4.02−4.17 (2H, t, Ar−O−CH$_2$), 4.58−4.68(1H, t,−COO−CH−), 6.63, 6.76, 7.06(3H, m, Ar−H) ppm; Mass m/z (rel. inten.): 276(30 M+), 122(50), 69(100), 55(60).

Example 5

Synthesis of 2,2-dimethyl-5-(2,5-dimethylphenoxy)-3-methoxypentanoic acid 2,2-Dimethyl-5(2,5-dimethylphenoxy)-3-hydroxypentanoic acid β-lactone (0.62 g, 2.5 mmol) and 3 ml of methanol were placed in a closed vessel and was heated at 130° C. After 7 days the mixture was partitioned with 20 ml of n-hexane and 20 ml of water containing 2.5 ml of 1 M sodium bicarbonate. The aqueous layer was separated, acidified to pH 3 with 1 M hydrochloric acid, and extracted with chloroform (3×10ml). The chloroform layer was dried with anhydrous magnesium sulfate and then filtered. The filtrate was concentrated by rotary evaporation to give 0.42 g of a crude product. The crude product was recrystallized from n-hexane to yield the product as white color solid, mp 76°−77° C. IR (KBr): 3500−2540 (Broad), 1703(Vc=o), 1616, 1586, 1510, cm$^{-1}$; $^1$H NMR (80 MHz, CDCl$_3$):Y 1.21−1.24(6H, d, −C(CH$_3$)$_2$−COO), 1.30−1.61(2H, m, Ar−O−CH$_2$−CH$_2$−), 2.18(3H, s, Ar−CH$_3$), 2.30(3H, s, Ar−CH$_3$), 3.45(3H, s, −OCH$_3$), 3.71(1H, dd, −CH(CH$_3$)−), 4.05(2H,dt, Ar−O−CH$_2$), 6.58, 6.65,(2H, d, Ar−H), 6.91, 7.01(1H, d, Ar−H) ppm; Mass m/z (rel. inten.): 280(41 M+), 193(61), 161(60), 159(48), 141(32), 135(58), 122(100), 105(25), 99(53),71 (57

Example 6

Synthesis of 2,2-dimethyl-5-(2,5-dimethylphenoxy)-3-ethoxypentanoic acid

The preparation was the same as in example 5, except that ethanol was used as solvent. After purification 0.31 g of the crude product was obtained. IR (KBr): 3500−2540 (Broad), 1703 (Vc=o), 1616, 1586, 1510, cm$^{-1}$; $^1$H NMR (80 MHz, CDCl$_3$):δ1.15(3H, t, −COO−CH$_2$CH$_3$), 1.24(6H, d, −C(CH$_3$)$_2$−COO), 1.81−2.09(2H, m, Ar−O−CH$_2$−CH$_2$), 2.17(3H, s, Ar−CH$_3$), 2.30 (3H, s, Ar−CH$_3$), 3.62 (2H, q, -OCH$_2$−CH$_3$), 3.78(1H, dd, −CH(OEt)−), 4.04(2H, dt, Ar−O−CH$_2$), 6.59, 6.68,(2H, d, Ar−H), 6.93, 7.03(1H, d, Ar−H) ppm; Mass m/z (rel. inten.): 294(19 M+), 207(11), 178(16), 173(29), 164(40), 145(22), 135(40), 122(73), 104(63), 78(64), 71(100).

Example 7

Synthesis of 3-acetoxy-2,2-dimethyl-5-(2,5-dimethylphenoxy)-pentanoic acid 2,2-Dimethyl-5 (2,5-dimethylphenoxy) -3-hydroxypentanoic acid β-lactone (2.48 g, 10 mmol) and sodium acetate (0.8 g) were dissolved in 30 ml of acetic acid. After refluxing for 24 hours, the acetic acid was removed in vacuo. The residue was dissolved in 20 ml of ethyl acetate and extracted with distilled water three times. The ethyl acetate was separated, dried, filtered and concentrated on a rotary evaporator. The crude product was recrystallized from n-hexane to give 2.83 g of the product as a solid, mp 92°−92.5° C. IR (KBr): 3731−2400 (broad), 1741 (Vc=o ester), 1708(Vc=o acid), 1616, 1586, 1510 cm$^{1}$; $^1$H NMR (80 MHz, CDCl$_3$): δ1.15(3H, t, −COO−CH$_2$CH$_3$), 1.26(6H, s, −C(CH$_3$)2−COO−), 2.05(3H, s, CH$_3$COO−), 2.16(6H, s, Ar−CH$_3$), 2.29(3H, s, Ar−CH$_3$), 3.93(2H, t, −Ar−O−CH$_2$−), 5.30−5.51(1H, q, −CH(OAc)−), 6.56, 6.66(2H, d, Ar−H), 6.92, 7.01 (1H, d, Ar−H), 8.95(1H, s, −COOH) ppm; Mass m/z (rel. inten.): 308(46 M+), 187(37), 161(52), 145(53), 135(13), 127(61), 122(100), 107(32), 99(57), 83(59), 70(79).

Examples 8 and 9

Synthesis of 3-pyridinylmethyl-2,2-dimethyl-5-(2,5-dimethyl-phenoxy)-3-hydroxy pentanoate (compound 8) and 2,2-dimethyl-5-(2,5-dimethylphenoxy)-3-(pyridinylmethoxy) pentanoic acid (compound 9)

2,2-Dimethyl-5(2,5-dimethylphenoxy)-3-hydroxypentanoic acid β-lactone (500 mg, 2 mmol) and nicotinyl alcohol (4.36 mg, 4 mmol) were dissolved in 5 ml of dioxane. Small amount of sodium hydride was added and the mixture was heated at 100° C. for 24 hours. Dioxane was evaporated and the residue was purified by column chromatography on silica gel to give two products. The first product did not dissolve in dilute sodium carbonate solution and was identified as compound 8 from the mass spectrum. The second product was soluble in dilute sodium carbonate solution and the mass spectrum confirmed the second product as compound 9. Mass m/z(rel. inten.) of compound 8: 357(M+,5), 341(4), 249(10), 148(30), 204(15), 178(20), 122(100), 92(5); of compound 9: 357(M+,22), 236(59), 179(18), 122(13), 108(8), 92(100).

Example 10

Synthesis of 3-[2(-4-chlorophenoxy)-2-methylpropionoxy]-2,2-dimethyl-5-(2,5 -dimethylphenoxy) pentanoic acid 2,2-Dimethyl-5(2,5-dimethylphenoxy)-3-hydroxypentanoic acid β-lactone (496.68 mg, 2 mmol) and 2-(4-chlorophenoxy)-2-methyl sodium propionate (517.9 mg, 2 mmol) were dissolved in 5 ml of dioxane and 44.05 mg (0.2 mmol) of 15-crown-5 was added as catalyst. After refluxing at 100° C. for 24 hours, the solution was partitioned with 20 ml of dilute HCl solution and 20 ml of n-hexane. The n-hexane layer was separated, dried with anhydrous magnesium sulfate and concentrated to give a crude solid. The crude solid was recrystallized from n-pentane to give the product as white needles, mp 119°−120° C. $^1$H NMR(80 MHz, CDCl$_3$):δ 1.22(6H, s−C(CH$_3$)2−COOH), 1.53(6H, S, Ar−O−CH$_3$ and Ar−O−CH$_2$−CH$_2$), 3.8−3.93(2H, q, Ar−OCH$_2$−), 5.47−5.61(1H, q, −COO−CH−), 6.0 (1H, broad, −COOH), 6.5−7.09 (7H, m, Ar−H) ppm; Mass m/z (rel. inten.): 462(M+,20), 341(35), 343(12), 248(7), 214(22), 169(33), 171(1), 122(100), 105(65), 77(35)

Example 11

Synthesis of 3-amino-2,2-dimethyl-5-(2,5-dimethylphenoxy) pentanoic acid 2,2-Dimethyl-5 (2,5-dimethylphenoxy) -3-hydroxy pentanoic acid β-lactone (0.50 g, 2 mmol) and ammonium acetate (0.17 g, 2.2 mmol) were dissolved in 5 ml of 1,4-dioxane. After refluxing for 24 hours, the solvent was removed under reduced pressure. The residue was recrystallized from water to give 0.37 g of the product as white solid (yield 72%), mp 86.1°−86.9° C. IR(KBr): 3450−3000(broad), 2975, 2925, 1655(VC=O), 1615, 1585, 1510, 1460, 1410 cm$^{-1}$; $^1$H NMR(80 MHz, CDCl$_3$): δ1.18(6H, d, −C(CH$_3$)2−COOH), 1.88−2.07(2H, m, Ar−O−CH$_2$−CH$_2$), 2.15, 2.19(6H, s, Ar−CH$_3$), 3.75, 3.78, 3.86, 3.9(1H, dd, −CH(NH2)−), 4.17(2H, m, Ar−O−CH$_2$), 6.65, 7.05(3H, m, Ar−H) ppm; Mass m/z: 266(4M+), 144(100), 135(3), 122(11), 107(5), 99(10), 87 (12).

Example 12

Synthesis of 5-(2,5-dimethylphenoxy) -3-hydroxy-2,2-dimethylpentanoic acid phenyl thioester 2,2-Dimethyl-5 (2,5-dimethylphenoxy) -3-hydroxypentanoic acid β-lactone (49.6 mg, 0.2 mmol) was dissolved in 5 ml anhydrous tetrahydrofuran. Thiophenol (122 mg, 0.2 mmol) and sodium hydride (4.8 mg, 0.2 mmol) were added. After stirring at room temperature for 24 hours, the mixture was partitioned with 50 ml of ethyl acetate and 50 ml of 1 M aqueous sodium carbonate solution. The organic layer was dried, evaporated and purified by column chromatography to give 44 mg of the product (yield 62%). $^1$H NMR(80 MHz, $CDCl_3$):δ1.30, 1.33(6H, s, $-C(CH_3)2$), 1.88–2.77(2H, m, $-CH_2-CH_2-CH_2$), 2.14(3H, s, $Ar-CH_3$), 2.27(3H, $Ar-CH_3$), 3.71–3.88(1H, dd, J=2.0, 11.5 Hz, HOCH–), 4.11–4.28(2H, m, $Ar-O-CH_2$), 6.51–7.4(8H, m, Ar–H) ppm; Mass(m/z): 358(76,M+), 121(23), 237 (57).

Example 13

Synthesis of 2,2-dimethyl-5-(2,5-dimethylphenoxy)-3-hydroxyhexanoic acid 2,2-Dimethyl-5-(2,5-dimethylphenoxy)-3-hydroxyhexanoic β-lactone (0.262 g, 1 mmol), was dissolved in 5 ml dimethyl formamide and 38 mg (1 mmol) of sodium borohydride was added at room temperature. After stirring for 12 hours, the solution was partitioned between 50 ml of 2M hydrochloric acid solution and 50 ml of n-hexane. The organic layer was separated, dried with anhydrous sodium sulfate and then filtered. The filtrate was concentrated under reduced pressure and purified by column chromatography to give 253 mg of the product (yield 96%). 1H NMR (80 MHz, $CDCl_3$): δ1.22(6H, s, $-C(CH_3)2-COO$), 1.32(3H, s, $Ar-O-CH_2-CH_3$), 1.68 (4H, $-CH_2-$), 2.14 (3H, s, $Ar-CH_3$), 2.28(3H, s, $Ar-CH_3$), 4.30(1H, b, Ar–O–CH), 6.56(1H, s, Ar–H), 6.59(1H, d, J=7.46 Hz, Ar–H), 6.96(1H, d, J=7.46 Hz, Ar–H), 8.55(1H, b, –COOH ) ppm.

Example 14

Synthesis of 2,2-direthyl-5-(2,5-dimethylphenoxy)-3-hydroxypentanoic acid

A mixture of 2,2 diethyl-5-(2,5-dimethylphenoxy)-3hydroxypentanoic acid lactone (1.10 g, 4 mmol) and sodium borohydride (0.15 g, 4 mmol) in DMF (5 mL) was stirred at room temperature for 20 h. DMF was removed in vacuo and water (50 ml) was added to the residue. The aqueous solution was carefully acidified with aqueous 3 M HCl solution and then extracted with n-hexane (2×50 mL). The n-hexane solution was dried with anhydrous $MgSO_4$ and filtered. The filtrate was concentrated in vacuo to give 1.07 g (96%) of the compound as white solid; mp 77°–78° C.; 1H NMR (80 MHZ, $CDCl_3$); δ0.89(6H, t, $-C(CH_2CH_3)2-COO-$), 1.71 (4H, q, $-C(CH_2CH_3)2-COO-$), 1.77(4H, s, $-CH_2-CH_2-CH_2-$), 2.11 (3H, s, $Ar-CH_3$), 3.96(2H, s, $Ar-O-CH_2$), 6.49–7.02 (3H, m, Ar–H ), 10.2 (1 H, s, COOH ) ppm.

Example 15

Determination of Anticholesteremic Activity

The compounds of the present invention are useful as anticholesteremic agents. This activity can be determined, for example, by the following procedure. This procedure is described in Evaluation of drug activity: Pharmacometrics, B. R. Laurance and A. L. Bacharac ed., Vol. II, Acad. Press, 1964, which is hereby incorporated by reference. Mice were injected with Triton WR-1399 to induce high content of cholesterol in their blood. These mice were then divided into several groups for drug treatment. Eight untreated mice were in the control group. Four mice were used in each drug treatment group.

The mice were fasted overnight, and were injected with 600 mg/kg Triton WR-199 (carried in physiological saline) through the tail vein. Each test drug was given orally (per os, or p.o.) or intraperitoneally (i.p.) at 100 mg/kg dosage (carried in 4 ml of 0.25% methyl cellulose solution) to each mouse group immediately or 20 hours following Triton introduction. Blood samples were collected through the carotid artery 43 hours after Triton introduction, and then were centrifuged, frozen for 40 to 50 minutes, and centrifuged again to obtain serum.

The serum cholesterol level of each sample was determined with a Technicon Autoanalyzer. Atromid (CPIP) 100 mg/kg was used as a positive control. Percentage of cholesterol reduction was determined by the following equation:

$$(AC-AT)/AC \times 100\% = \% \text{ reduction}$$

wherein AC is an average cholesterol level in control group (mg %); and AT is an average cholesterol level in test group (mg %).

TABLE 1

| Compound | Dose (mg/kg) | Route | Reduction of Blood Cholesterol (%) |
|---|---|---|---|
| gemfibrozil | 100 | p.o. | 5% |
| gemfibrozil | 100 | i.p. | 30% |
| 6 | 100 | p.o. | 17% |
| 7 | 100 | p.o. | 11% |
| 7 | 100 | i.p. | 25% |
| 14 | 100 | i.p. | 22% |

The results indicated that the compounds of the present invention had greater activity in reducing blood cholesterol levels than the commercially available drug gemfibrozil.

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound of the following formula:

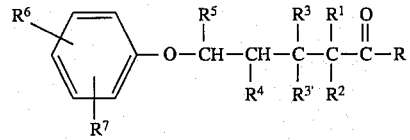

wherein R is hydroxy, $C_1-C_8$ alkoxy, phenoxy, $C_1-C_4$ alkylthio, phenylthio, amino, $C_1-C_4$ alkylamino, phenylamino, benzylamino, or pyridyl-3-methoxy; each of $R^1$ and $R^2$ independently is hydrogen, or $C_1-C_4$ alkyl; $R^3$ is $C_1-C_8$ alkoxy, $C_1-C_5$ acyloxy, pyridyl-3-methoxy, $C_1-C_4$ alkylthio, phenylthio, amino, $C_1-C_4$ alkylamino, phenylamino, benzylamino, $C_2-C_5$ alkylacyl, or $C_7-C_{10}$ phenylacyl,

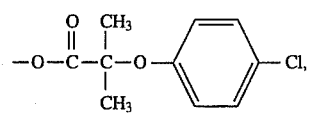

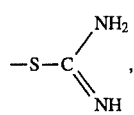

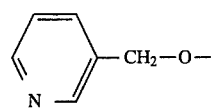

or

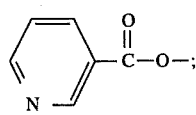

each of $R^3$, $R^4$ and $R^5$ independently is hydrogen or $C_1$–$C_4$ alkyl; and each of $R^6$ and $R^7$ independently is hydrogen, hydroxy, halogen, $C_1$–$C_8$ alkyl, $C_1$–$C_8$ alkoxy, $C_1$–$C_8$ acyl, or $C_1$–$C_8$ alkylamino.

2. The compound of claim 1, wherein each of $R^1$ and $R^2$ independently is $C_1$–$C_4$ alkyl.

3. The compound of claim 1, wherein $R^3$ is $C_1$–$C_8$ alkoxy, or $C_1$–$C_5$ acyloxy.

4. The compound of claim 1, wherein each of $R^{3'}$, $R^4$ and $R^5$ independently is $C_1$–$C_4$ alkyl.

5. The compound of claim 4, wherein each of $R^{3°}$, $R^4$ and $R^5$ independently is methyl.

6. The compound of claim 1, wherein each of $R^6$ and $R^7$ independently is hydrogen, hydroxy, halogen, or $C_1$–$C_4$ alkyl.

7. A compound of the following formula:

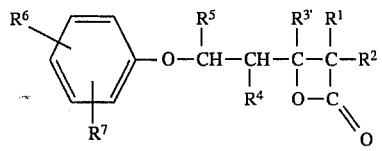

wherein and each of $R^1$, $R^2$, $R^4$ and $R^5$ independently is hydrogen or $C_1$–$C_4$ alkyl; $R^{3'}$ is $C_1$–$C_4$ alkyl; each of $R^6$ and $R^7$ independently is hydrogen, hydroxy, halogen, $C_1$–$C_8$ alkyl, $C_1$–$C_8$ alkoxy, $C_1$–$C_8$ acyl, or $C_1$–$C_8$ alkylamino.

8. The compound of claim 7, wherein each of $R^1$ and $R^2$ independently is $C_1$–$C_4$ alkyl.

9. The compound of claim 7, wherein each of $R^{3'}$, $R^4$ and $R^5$ independently is $C_1$–$C_4$ alkyl.

10. The compound of claim 7, wherein each of $R^{3'}$, $R^4$ and $R^5$ independently is methyl.

11. The compound of claim 7, wherein each of $R^6$ and $R^7$ independently is hydrogen, or methyl.

12. A method for preparing a compound of the following formula

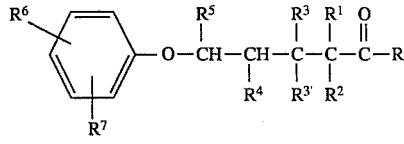

wherein R is hydroxy, $C_1$–$C_8$ alkoxy, phenoxy, $C_1$–$C_4$ alkylthio, phenylthio, amino, $C_1$–$C_4$ alkylamino, phenylamino, benzylamino, or pyridyl-3-methoxy; each of $R^1$ and $R^2$ independently is hydrogen or $C_1$–$C_4$ alkyl; $R^3$ is $C_1$–$C_8$ alkoxy, $C_1$–$C_5$ acyloxy, pyridyl-3-methoxy, $C_1$–$C_4$ alkylthio, phenylthio, amino, $C_1$–$C_4$ alkylamino, phenylamino, benzylamino, $C_2$–$C_5$ alkylacyl, or $C_7$–$C_{10}$ phenylacyl,

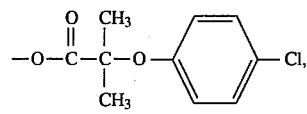

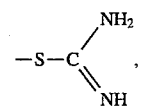

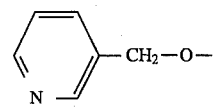

or

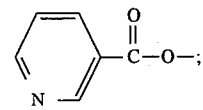

each of $R^{3'}$, $R^4$ and $R^5$ independently is hydrogen or $C_1$–$C_4$ alkyl; and each of $R^6$ and $R^7$ independently is hydrogen, hydroxy, halogen, $C_1$–$C_8$ alkyl, $C_1$–$C_8$ alkoxy, $C_1$–$C_8$ acyl, or $C_1$–$C_8$ alkylamino; which method comprises reacting a compound of the following formula

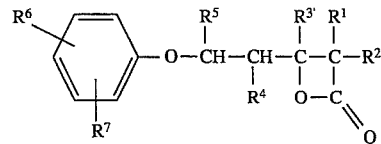

wherein each of $R^1$, $R^2$, $R^{3'}$, $R^4$ and $R^5$ independently is hydrogen, or $C_1$–$C_4$ alkyl; each of $R^6$ and $R^7$ independently is hydrogen, hydroxy, halogen, $C_1$–$C_8$ alkyl, $C_1$–$C_8$ alkoxy, $C_1$–$C_8$ alkylacyl, or $C_1$–$C_8$ alkylamino, with (1) $C_1$–$C_8$ alkyl alcohol, $C_1$–$C_4$ alkylthiol, thiophenol, ammonia, $C_1$–$C_8$ alkylamine, aniline, benzylamine, $C_1$–$C_9$ aliphatic acid, thiourea, 3-hydroxymethyl pyridine, nicotinic acid, or $C_7$–$C_{11}$ phenylaliphatic acid or $C_7$–$C_{11}$ alkylbenzoic acid, in the presence of aliphatic alcohol or an alkyl benzene solvent, or (2) sodium borohydride in a polar aprotic solvent.

13. The method of claim 12, wherein said aliphatic alcohol is propyl alcohol, or n-butyl alcohol.

14. The method of claim 12, wherein said alkyl benzene is toluene, or dimethyl benzene.

15. The method of claim 12, wherein said polar protic solvent is acetic acid, or $C_2$–$C_4$ alkylalcohol.

16. The method of claim 12, wherein said polar aprotic solvent is tetrahydrofuran, 1,2-dimethoxy ethane, or dimethylfuran.

17. A method for preparing a compound of the following formula

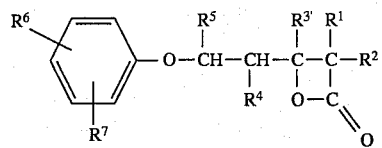

wherein and each of $R^1$, $R^2$, $R^4$ and $R^5$ independently is hydrogen or $C_1$–$C_4$ alkyl; $R^{3'}$ is $C_1$–$C_4$ alkyl; each of $R^6$ and $R^7$ independently is hydrogen, hydroxy, halogen, $C_1$–$C_8$ alkyl, $C_1$–$C_8$ alkoxy, $C_1$–$C_8$ alkylacyl, or $C_1$–$C_8$ alkylamino; which method comprises reacting a compound of the following formula

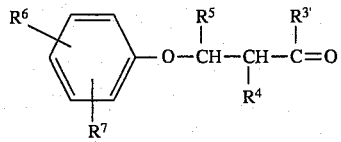

wherein $R^{3'}$, $R^4$, $R^5$, $R^6$ and $R^7$ are as defined above with $C_3$–$C_6$ alkylketene or $C_4$–$C_{10}$ dialkylketene in the presence of Lewis acid in an aprotic organic solvent or in polar aprotic solvent.

18. The method of claim 17, wherein said aprotic organic solvent is dichloromethane, carbon tetrachloride, methyl acetate, ethyl acetate, or 1,2-dimethoxy ethane.

19. The method of claim 17, wherein said polar aprotic solvent is hexamethylphosphoramide, N,N-dimetylformamide, dimetylsulfoxide, or N,N-dimetylacetamide.

20. The method of claim 17, wherein said Lewis acid is zinc (II) chloride, aluminum (III) chloride, iron (III) chloride, titanium (IV) chloride, titanium (IV) tetraalkoxide, boric acid, boron trifluoride, trialkyl borate, zirconium (IV) tetrachloride, or zirconium (IV) tetralkoxide.

* * * * *